United States Patent
Wang et al.

(10) Patent No.: US 12,151,074 B2
(45) Date of Patent: Nov. 26, 2024

(54) POLYMER MICRONEEDLE MEDIATED DRUG DELIVERY

(71) Applicant: The Penn State Research Foundation, University Park, PA (US)

(72) Inventors: Yong Wang, State College, PA (US); James Coyne, State College, PA (US); David Kauffman, Ambler, PA (US); Brandon Davis, Yardley, PA (US)

(73) Assignee: The Penn State Research Foundation, University Park, PA (US)

(*) Notice: Subject to any disclaimer, the term of this patent is extended or adjusted under 35 U.S.C. 154(b) by 913 days.

(21) Appl. No.: 17/271,486

(22) PCT Filed: Aug. 27, 2019

(86) PCT No.: PCT/US2019/048242
§ 371 (c)(1),
(2) Date: Feb. 25, 2021

(87) PCT Pub. No.: WO2020/046863
PCT Pub. Date: Mar. 5, 2020

(65) Prior Publication Data
US 2021/0196939 A1 Jul. 1, 2021

Related U.S. Application Data

(60) Provisional application No. 62/725,348, filed on Aug. 31, 2018.

(51) Int. Cl.
*A61M 37/00* (2006.01)
*A61K 9/00* (2006.01)
(Continued)

(52) U.S. Cl.
CPC ....... *A61M 37/0015* (2013.01); *A61K 9/0021* (2013.01); *A61K 38/1866* (2013.01);
(Continued)

(58) Field of Classification Search
CPC ...... A61M 37/0015; A61M 2037/0023; A61M 2037/0046; A61M 2037/0053;
(Continued)

(56) References Cited

U.S. PATENT DOCUMENTS

| | | | |
|---|---|---|---|
| 2013/0196915 A1* | 8/2013 | Wang | A61K 38/27 514/11.3 |
| 2013/0338632 A1 | 12/2013 | Kaplan et al. | |
| 2017/0298343 A1 | 10/2017 | Mayer et al. | |

FOREIGN PATENT DOCUMENTS

WO 2018165294 A1 9/2018

OTHER PUBLICATIONS

Han et al., "In situ cross-linkable hyaluronic acid hydrogels using copper free click chemistry for cartilage tissue engineering", Polym. Chem., 2018, vol. 9, No. 1, pp. 20-27. First published Oct. 2017. (Year: 2017).*

(Continued)

*Primary Examiner* — Benjamin J Packard
*Assistant Examiner* — Joshua A Atkinson
(74) *Attorney, Agent, or Firm* — DINSMORE & SHOHL LLP

(57) ABSTRACT

A method of providing therapeutic treatment by delivering therapeutic aptamers locally to a target site using microneedles includes providing complementary sequence modified microneedles by reacting a complementary sequence (CS) with a polymer thereby forming a covalent bond between the polymer and the CS, forming microneedle patches using an initial casting solution consisting of the polymer, the therapeutic aptamer, and a covalent bond between a complementary sequence (CS) and the polymer, thereby loading the therapeutic aptamer into the microneedles, each microneedle having a base, shaft and tip, physically binding the therapeutic aptamer to the CS, inserting the microneedles into the tissue such that the tips and (Continued)

shafts are embedded into the target site and the bases are on a surface of the target site, and sustained release of the aptamer to the target site due to dissociation of the aptamer from the CS over time.

7 Claims, 10 Drawing Sheets

(51) Int. Cl.
    *A61K 38/18*     (2006.01)
    *A61K 47/32*     (2006.01)
    *A61K 47/61*     (2017.01)
    *C12N 15/115*     (2010.01)

(52) U.S. Cl.
    CPC .............. *A61K 47/32* (2013.01); *A61K 47/61* (2017.08); *A61M 2037/0023* (2013.01); *A61M 2037/0046* (2013.01); *A61M 2037/0053* (2013.01); *A61M 2037/0061* (2013.01); *A61M 2202/0445* (2013.01); *A61M 2210/04* (2013.01); *A61M 2210/0612* (2013.01); *A61M 2210/125* (2013.01); *C12N 15/115* (2013.01)

(58) Field of Classification Search
    CPC ......... A61M 2037/0061; A61K 9/0021; A61K 38/1866; A61K 47/32; A61K 47/61; A61K 31/7088; C12N 15/115; C12N 15/89; A61B 17/205; B82Y 5/00
See application file for complete search history.

(56) References Cited

OTHER PUBLICATIONS

Coyne et al. "Polymer Microneedle Mediated Local Aptamer Delivery for Blocking the Function of Vascular Endothelial Growth Factor," ACS Biomater Sci Eng, Oct. 31, 2017 (Oct. 31, 2017), vol. 3, Iss. 12, pp. 3395-3403. entire document.
Lim et al. "Response to di-functionalized hyaluronic acid with orthogonal chemistry grafting at independent modification sites in rodent models of neural differentiation and spinal cord injury," Journal of Materials Chemistry B, Sep. 26, 2016 (Sep. 26, 2016), vol. 2016, Iss. 4, pp. 6865-6875. entire document.
International Search Report dated Nov. 15, 2019; International Application No. PCT/US2019/048242.
Lee, K.J., S.H. Park, J.Y. Lee, H.C. Joo, E.H. Jang, Y.-N. Youn, W. Ryu, Perivascular biodegradable microneedle cuff for reduction of neointima formation after vascular injury, J. Control. Release. 192 (2014) 174-181, https://doi.org/ https://doi.org/10.1016/j.jconrel.2014.07.007 <https://protect-us.mimecast.com/s/PS0vCKr6loT0PNKXuv9x1k?domain=nam10.safelinks.protection.outlook.com>.
Tang, J, Wang, K. Huang, Y. Ye, T. Su, L. Qiao, M.T. Hensley, T.G. Caranasos, J. Zhang, Z. Gu, K. Cheng, Cardiac cell-integrated microneedle patch for treating myocardial infarction, Sci. Adv. 4 (2018), https://doi.org/10.1126/sciadv.aat9365 <https://protect-us.mimecast.com/s/K3uSCM89nqsGD1PwuWWe4P?domain=nam10.safelinks.protection.outlook.com>.
Post Mark J. et al.; Therapeutic angiogenesis in cardiology using protein formulations. Cardiovascular Research 49 (2001) 522-531.
Gnann et al.; Hematological and hepatic effects of vascular epidermal growth factor (VEGF) used to stimulate hair growth in an animal model; BMC Dermatology 2013, 13:15 http://www.biomedcentral.com/1471-5945/13/15.

\* cited by examiner

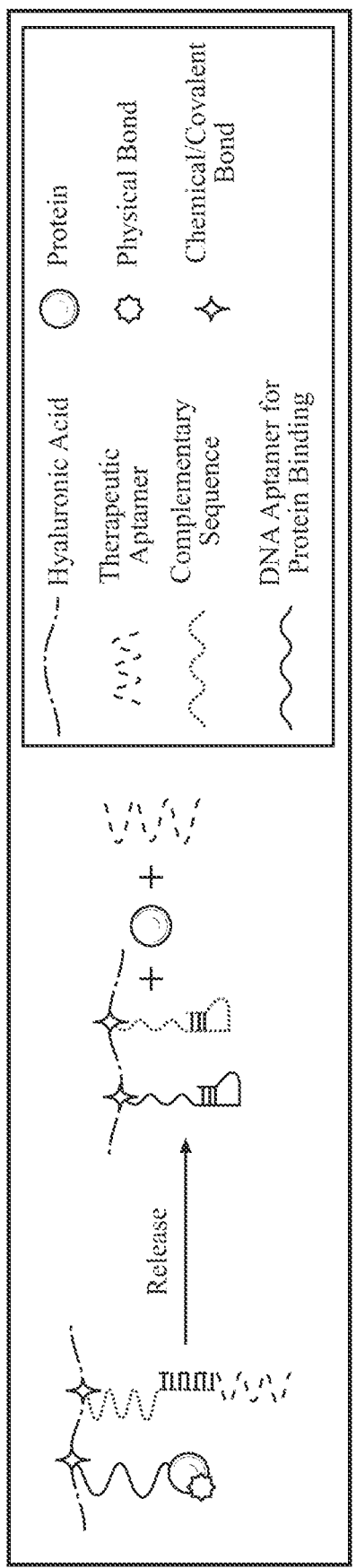
FIG. 2C
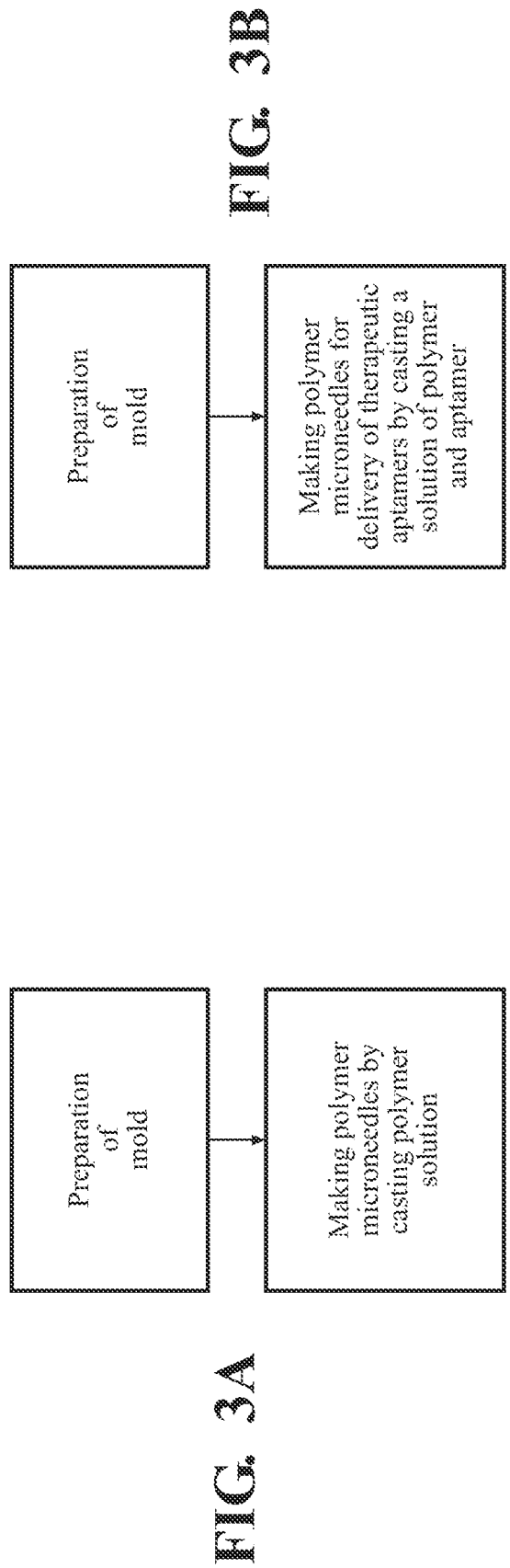
FIG. 3A
FIG. 3B

FIG. 6A
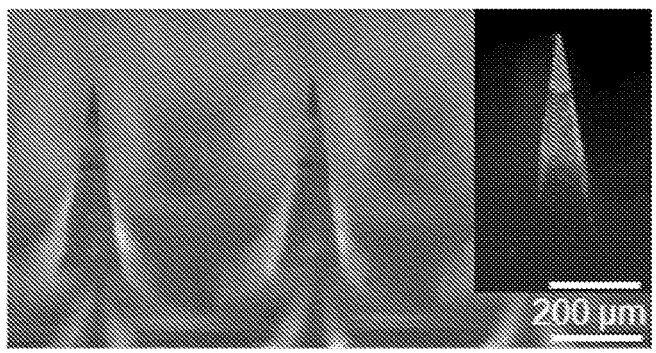
FIG. 6B
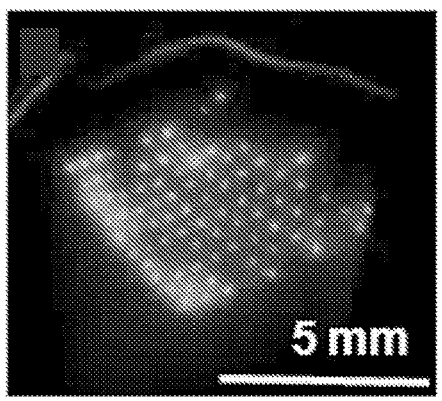
FIG. 6C
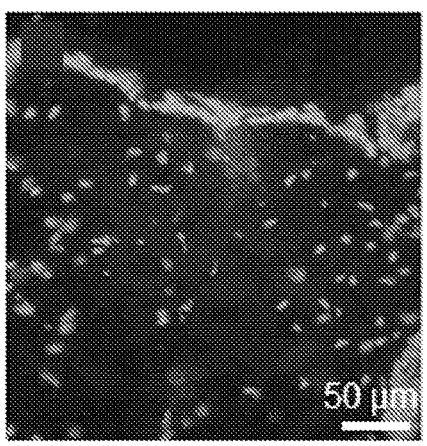
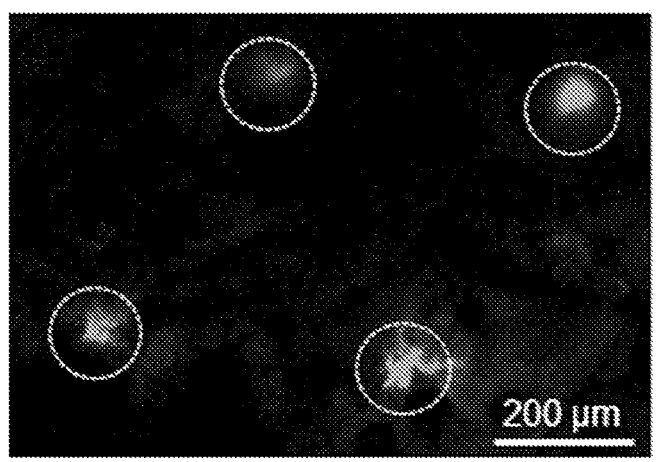
FIG. 6D

POLYMER MICRONEEDLE MEDIATED DRUG DELIVERY

CROSS REFERENCE TO RELATED APPLICATION

This application is the U.S. National Stage of PCT/US2019/048242 filed Aug. 27, 2019, which claims priority to U.S. Provisional Patent Application Ser. No. 62/725,348, filed Aug. 31, 2018, the entire content of both are incorporated herein by reference in their entirety.

GOVERNMENT SUPPORT

This invention was made with government support under Grant No. HL122311 awarded by the National Institutes of Health. The Government has certain rights in the invention.

FIELD OF THE INVENTION

The present invention relates to the delivery of therapeutic agents (growth factors, nucleic acids, or other drugs) by polymer microneedles for treatment of heart disease and skin or eye diseases.

BACKGROUND OF THE INVENTION

Approximately 8% of Americans aged 18 and older have coronary artery disease. It is the leading cause of death in the United States. It is characterized by the narrowing of the epicardial coronary arteries. While a variety of therapeutic agents (e.g., growth factors, nucleic acids and stem cells) have been rigorously studied, their delivery into the diseased heart remains a huge challenge. Intramyocardial injection has the following problems: 1) the injection into the deep regions of heart is invasive; 2) it requires highly specialized equipment and a higher skill level of operator; 3) it does not help the induction of arteriogenesis of the epicardial vessels that are the origin of the disease; and 4) intramyocardial injection cannot provide a uniform distribution of therapeutic agents in the diseased site. Alternatively, suturing an implant on the surface of the heart has also been studied. However, this method is inherently associated with the problems including 1) the sutures can damage the surrounding normal heart tissues particularly because the heart is a beating organ with cyclic expansion and shrinkage; and 2) suturing an implant on the surface of a beating heart requires a very high skill level of operation, which is also time-consuming with more danger to a patient during the operation.

For another example, approximately ⅔ of American men will experience hair loss by the age of thirty five and 85% by the age of fifty. The major reason for hair loss is the insufficient supply of nutrients to hair follicles owing to the shortage of blood flow in the areas surrounding hair follicles. Thus, the treatment of the scalp using angiogenic factors is a right solution. Indeed, the ability to increase the expression of VEGF has demonstrated the effectiveness of promoting hair growth and preventing hair loss. However, oral administration of pills (e.g., PriaPlex) to promote hair growth takes too long (e.g., one to two years in general) for therapeutic effects. Moreover, the systemic drug distribution may lead to unnecessary growth of blood vessels in other tissues with systemic side effects (e.g., induction of cancer). Alternatively, VEGF can be administered locally to the bald area. However, VEGF is a large biomolecule that cannot penetrate the dense scalp.

SUMMARY OF THE INVENTION

An embodiment of the present invention provides a method of providing therapeutic treatment by delivering therapeutic aptamers locally to a target site using complementary sequence modified microneedles. The complementary sequence modified microneedles may be formed using an initial casting solution consisting of the polymer, the therapeutic aptamer, and the covalent bond polymer-CS between the complementary sequence (CS) and the polymer. In this case, a complementary sequence is chemically conjugated to the polymer matrix of the microneedles forming a covalent bond and is acting as a binding site for the therapeutic aptamers.

In one example, the CS and polymer are first mixed together and reacted to form a conjugate. Then the polymer-CS, aptamer, and polymer are added as the initial casting solution. More polymer will be added after the conjugate is formed. The polymer-CS conjugate will only be a certain percentage of the total polymer amount.

In another example, the CS, polymer and aptamer all added together. After the polymer-CS conjugate is formed, more polymer may be added.

Each microneedle may include a base, shaft and tip. The therapeutic aptamer may physically bind to the CS. When the microneedles are inserted into the tissue such that the tips and shafts are embedded into the target site and the bases are on a surface of the target site, the aptamers may be sustainably released to the target site due to dissociation of the aptamer from the CS over time. The sustained release of the aptamers is due to the hybridization kinetics between the therapeutic aptamer and CS. The degree of hybridization can be controlled by modifying the number of base pairs of the CS and aptamer duplex. The dissociation may take place prior to, during or after dissolution or degradation of the microneedles. The aptamer may be further released by dissolution or degradation of the microneedles.

In one example, the CS is an azide-modified CS, the polymer is hyaluronic acid functionalized with methacrylate and DBCO (mHA-DBCO), and the covalent bond is mHA-CS. The DBCO moiety is no longer present after the reaction with azide.

In another example, the CS is an azide-modified CS, the polymer is hyaluronic acid functionalized with DBCO (HA-DBCO), and the covalent bond is HA-CS.

Depending on the method of molding the microneedles, the aptamer may be loaded into the tips, shafts or bases of the microneedles. The term "loaded" or "loading" means that the aptmer is present in and forms the part of the tips, shafts or bases of the microneedles. The target site may be heart tissue, skin or eye or other tissue locations suitable for the microneedle treatment.

Another embodiment of the present invention provides a method of providing therapeutic treatment by delivering protein locally to a target site using aptamer-functionalized microneedles. The aptamer-functionalized microneedles may be formed using an initial casting solution consisting of the polymer, the protein and the covalent bond between the polymer and the aptamer. The protein may physically bind to the aptamer. When the microneedles are inserted into the tissue such that the tips and shafts are embedded into the target site and the bases are on a surface of the target site, the protein may be released to the target site due to dissociation of the protein from the aptamer for an extended period of time. The dissociation may take place prior to, during or after dissolution or degradation of the microneedles.

The protein release profile is mainly governed by the aptamer-protein binding strength (affinity). The binding effect is also affected by the protein concentration, aptamer concentration, and the ion concentration. These concentrations will change over time causing protein dissociation. The protein is constantly binding and re-binding with the aptamer. An aptamer with a high affinity will be able to hold on to the protein for a longer time than a lower affinity aptamer. The aptamer is "anchored" to the microneedle to provide a high local concentration of binding sites of the protein, providing a "slow" protein release.

The dissociation may take place prior to, during or after dissolution or degradation of the microneedles. The cross-linked, aptamer-functionalized polymer may also be gradually hydrolyzed and/or dissolved in the body, which may facilitate the release kinetics of loaded proteins. The term "loaded" or "loading" means that the protein is present in and forms the part of the tips, shafts or bases of the microneedles.

In one example, the polymer is the hyaluronic acid functionalized with methacrylate and DBCO (mHA-DBCO), the aptamer is azide-modified DNA aptamer and the covalent bond is formed through DBCO-azide click chemistry to form an mHA-Apt conjugate.

In another example, the polymer is the hyaluronic acid functionalized with DBCO (HA-DBCO), the aptamer is azide-modified DNA aptamer and the covalent bond is formed through DBCO-azide click chemistry to form an HA-Apt conjugate.

Another embodiment of the present invention provides a method of providing therapeutic treatment by delivering protein to a target site locally using protein-loaded microneedles. The protein-loaded microneedles may be formed using an initial casting solution consisting of the polymer, the protein and aptamer-functionalized nanoparticles. The protein may physically bond to the aptamer of the aptamer-functionalized nanoparticles. When the protein-loaded microneedles are inserted the microneedles into the target site such that the tips and shafts of the microneedles are embedded into the target site and the bases of the microneedles are on a surface of the target site, the protein may be slowly released to the target site due to dissociation of the protein from the aptamer over time. The dissociation may take place prior to, during or after dissolution or degradation of the microneedles. The protein can also be further released by dissolution or degradation of the microneedles.

In an example, the polymer used in this method is polyvinylpyrrolidone/polyvinyl alcohol (PVA/PVP).

BRIEF DESCRIPTION OF THE INVENTION

FIG. 2C is a schematic showing the mechanism of protein delivery using aptamers and delivery of therapeutic aptamers using a complementary sequence at the same time;

FIG. 3A is a flowchart showing a method of making polymer microneedle patches in accordance with an embodiment of the present invention;

FIG. 3B is a flowchart showing a method of incorporation of therapeutic aptamers into microneedles;

Figure 4A:
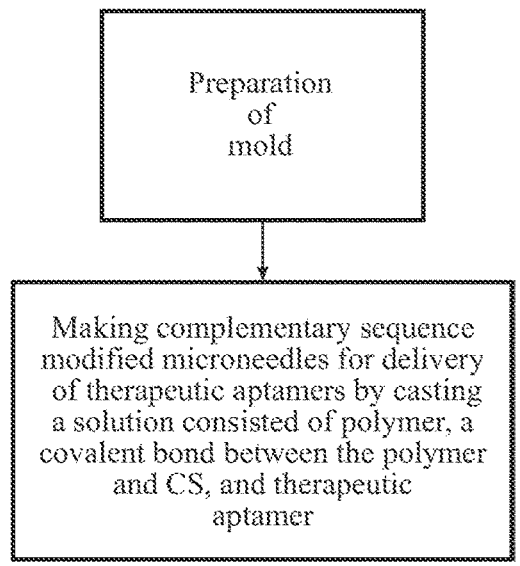
FIG. 4A is a flowchart showing a method of incorporation of therapeutic aptamers into complementary sequence modified microneedles.
Figure 4B:
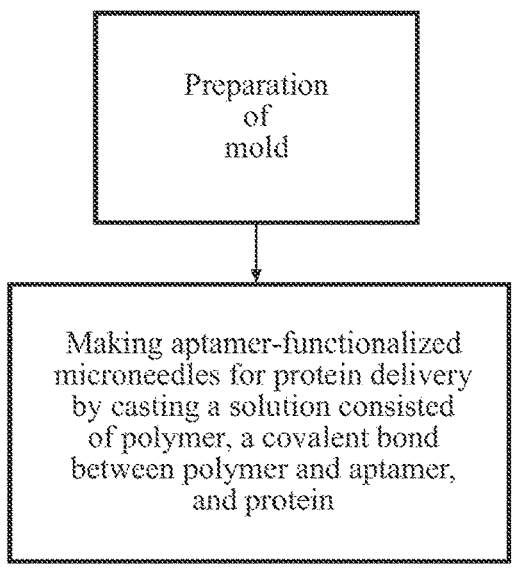
Figure 5A:
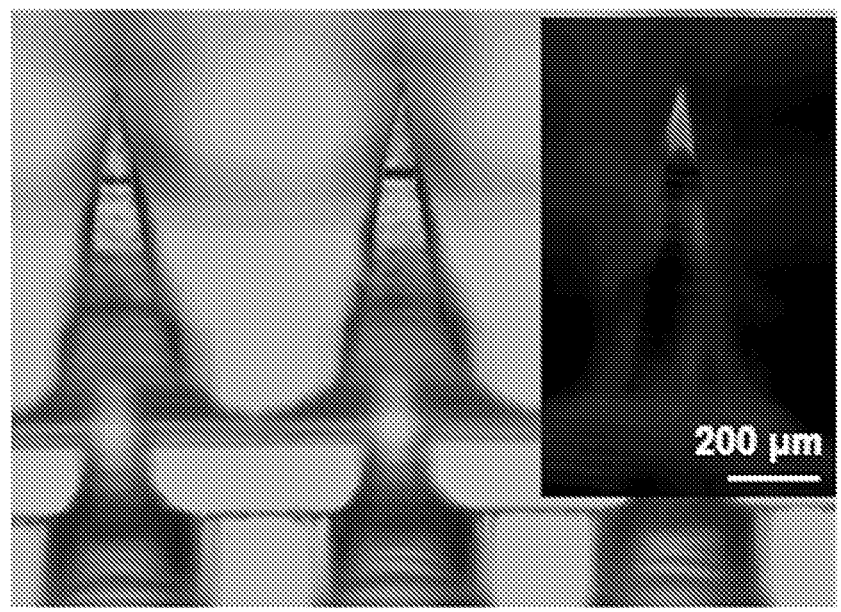
Figure 5B:
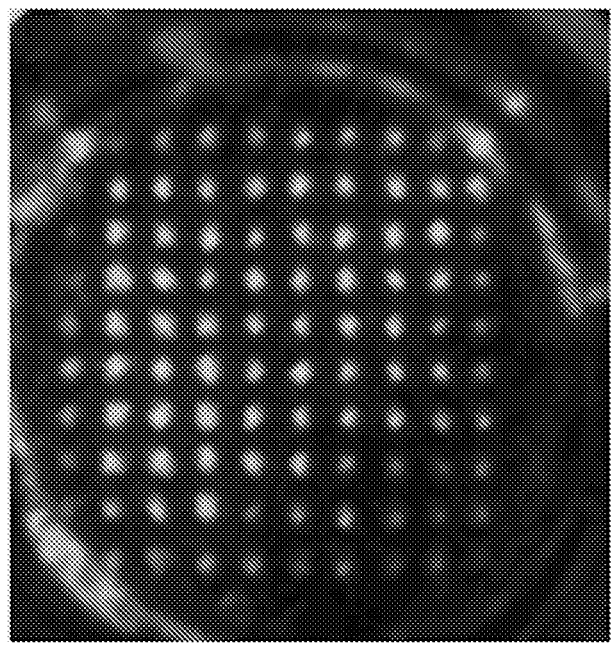
Figure 7A:
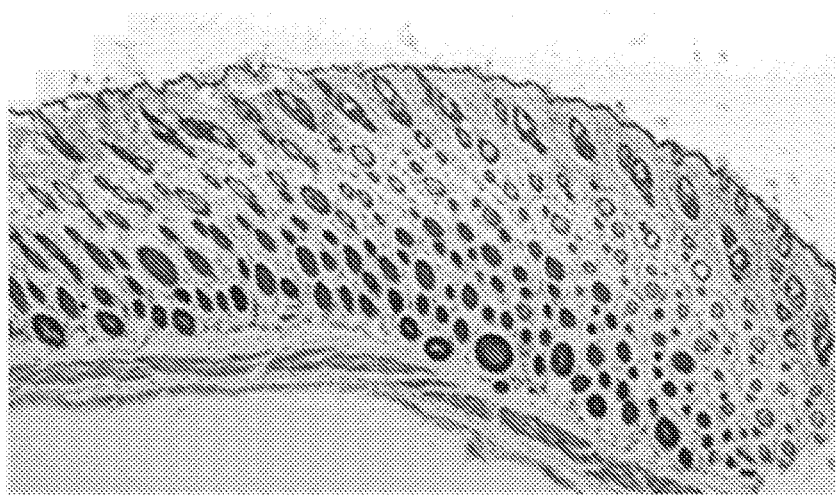
Figure 7B:
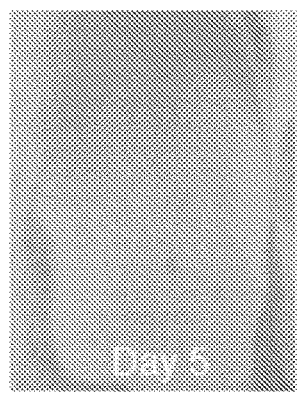
Figure 7C:
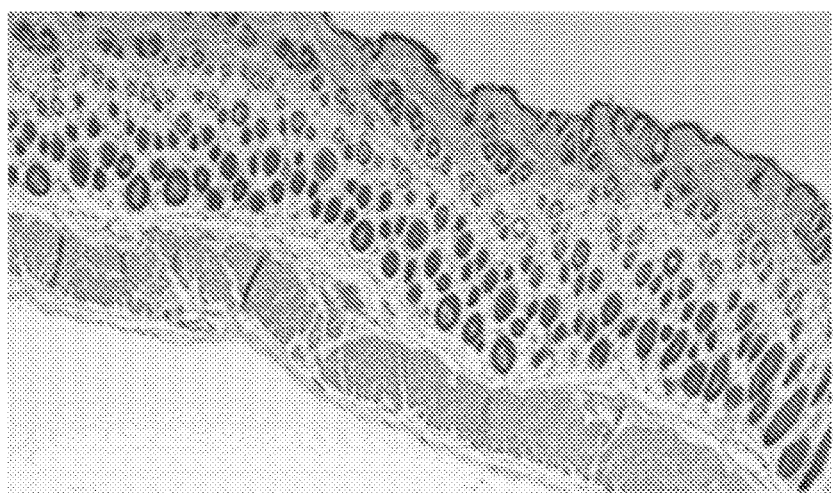
Figure 7D:
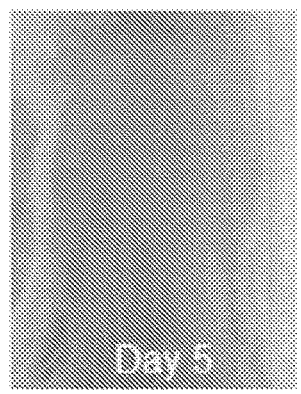
Figure 8A:
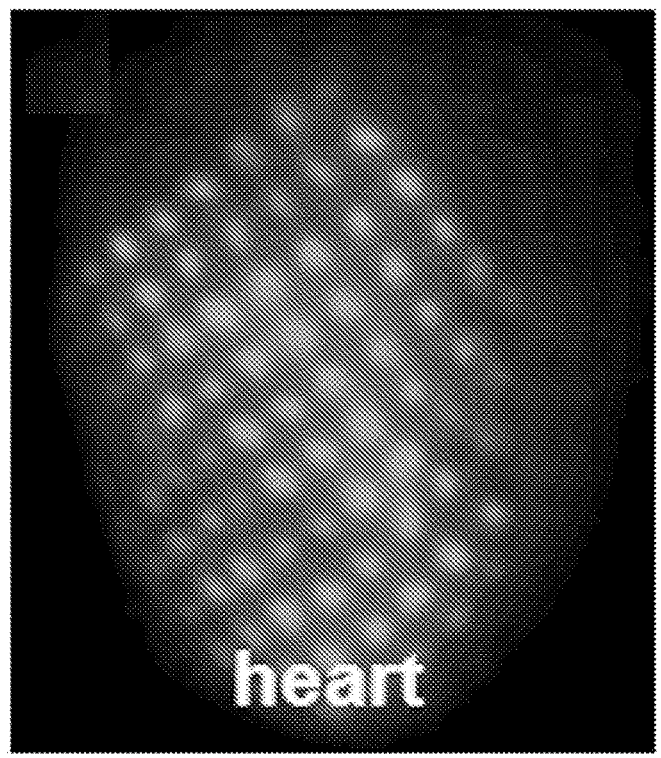
Figure 8B:
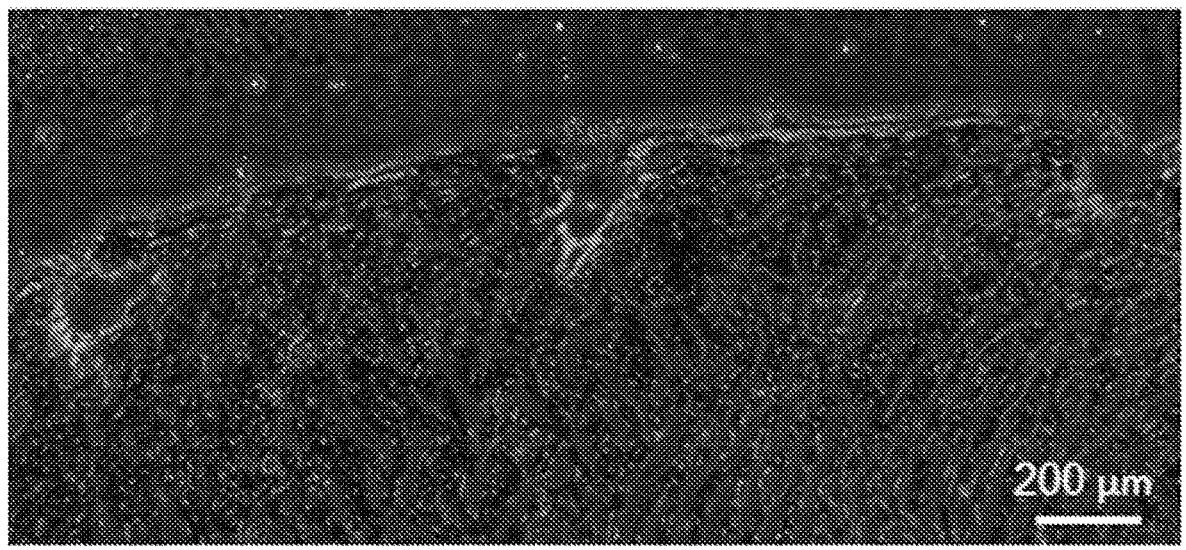

FIG. 4B a flowchart showing a method of incorporation of proteins into aptamer-functionalized microneedles for protein delivery;

FIG. 5A is a bright-field image of a microneedle array and the inset is a fluorescent image of microneedles loaded with nanoparticles;

FIG. 5B is an image of nanoparticle deposition after microneedle insertion into a tissue phantom;

FIGS. 6A-6D are images showing examination of protein-loaded microneedles;

FIGS. 7A-7D are images showing examination of hair growth treatment using VEGF-loaded microneedles; and FIGS. 8A-8B are images showing examination of microneedle insertion into the mouse heart.

DETAILED DESCRIPTION OF THE INVENTION

The present invention provides a plurality of methods for delivering aptamers or proteins to a target site locally for treatment. The target site may be heart, skin or eye, or any other tissues that are suitable for this treatment method. The present invention also provides methods for fabricating the microneedles used for each different method for delivering aptamers or protein. Each method will be described in detail below.

Method 1

1.1 Preparation of Mold

In this example, pyramidal master structures were obtained from Micropoint Technologies Pte, Ltd., Singapore. Each microneedle array consisted of 100 (10×10) pyramidal microneedles with a height, base, and tip-to-tip distance of 600 μm, 200 μm, and 500 μm, respectively. Female microneedles molds were made by casting PDMS into the master structures and allowing the PDMS solution to cure overnight at 37° C.

1.2 General Procedure of Making Microneedle Patches

In this example, the polymer microneedle arrays can be fabricated. Polyvinyl alcohol (PVA) and polyvinylpyrrolidone (PVP) are used to fabricate the microneedle array. In brief, 3 g of polyvinyl alcohol (PVA, Sigma Aldrich 10K) is mixed with 4 mL of water and heated to 90° C. for 2 hours. 1 g of polyvinylpyrrolidone (PVP, Sigma Aldrich 10K) is added into the PVA solution and the mixture is heated at 90° C. for another 2 hours. 5 μL of the PVA/PVP solution (20% w/v) is cast into the PDMS mold to fabricate polymer microneedles. The PDMS mold is placed in a vacuum chamber for 2 minutes and centrifuged for 10 minutes at 3000 RCF (relative centrifugal force). Excess polymer may be removed and the process may be repeated 3 times to ensure all the microneedle cavities are full. After the microneedles are dried for a half-hour, 50 µL of the PVA/PVP solution (50% w/v) is cast on the top of the microneedle array as a base plate and dried for 48 hours to form the final microneedle array. This method is summarized in FIG. 3A.

1.3 Method 1 for Delivery of Therapeutic Aptamer

This method includes the steps of preparing a mold using the method described above in 1.1 and then making polymer microneedles for delivery of therapeutic aptamers by casting a solution consisted of the polymer and the aptamer, as shown in FIG. 3B.

In an example, the microneedle patches for delivery of therapeutic aptamer can be made using the procedure as described in 1.2, except that the initial casting solution of PVA/PVP was replaced with PVA/PVP and aptamers.

1.4 Method 1 for Protein Delivery

Figure 3C:
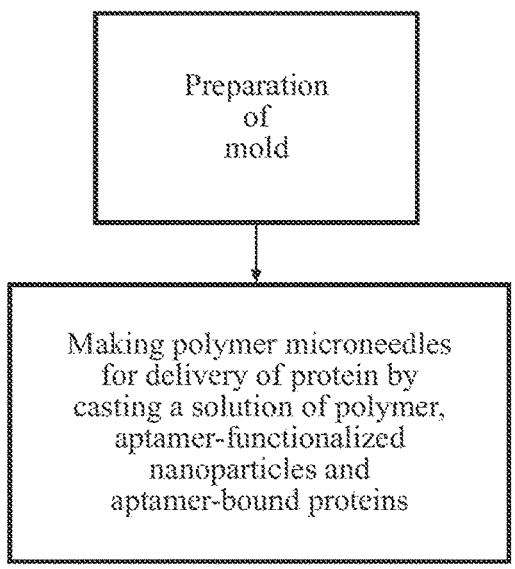
FIG. 3C is a flowchart showing a method of incorporation of aptamer-functionalized nanoparticles and proteins into microneedles for protein delivery.

This method includes the steps of preparing a mold using the method described above in 1.1 and then making polymer microneedles for delivery of protein by casting a solution consisted of the polymer, the aptamer-functionalized nanoparticles and aptamer-bound protein, as shown in FIG. 3C.

In an example, the procedure as shown in 1.2 can be used except that the initial casting solution of PVA/PVP is replaced with PVA/PVP, aptamer-functionalized nanoparticles and aptamer-bound proteins such that incorporation of aptamer-functionalized nanoparticles and proteins into microneedles is achieved for protein delivery.

Method 2

2.1 Preparation of Mold

A mold may be prepared using the method described in 1.1.

2.2 Procedures of Making Microneedles for Delivery of Protein or Therapeutic Aptamers Two examples will be given to describe how the microneedles are fabricated for delivery of protein and therapeutic aptamers.

Example 1

2.2.1 General Procedure of Making Microneedle Patches

In this example, the polymer microneedles are fabricated by casting 20 µL of mHA-DBCO (1 wt %) dissolved in a solution containing N',N'-methylenebis (acrylamide) (1 wt %) and Irgacure 2959 (0.1 wt %). The microneedle mold is placed in a vacuum chamber for 10 minutes and then centrifuged for 10 minutes at 3000 RCF (relative centrifugal force). Excess polymer may be removed and the process may be repeated three times to ensure all the microneedle cavities are full. After drying, the microneedle molds are exposed to UV light (365 nm) for 2 minutes to initiate crosslinking. Then, 100 µL of HA (4 wt %) is cast to form the microneedle shafts followed by the casting of PVA/PVP to form the microneedle base.

2.2.2. Method 2 for Delivery of Therapeutic Aptamer

An azide-modified complementary sequence (CS) that is capable of physically binding to the therapeutic aptamer, is reacted with mHA-DBCO. The reaction results in a covalent bond between the polymer and complementary sequence to form a conjugate (i.e., mHA-CS). The above procedure as shown in 2.2.1 may be used except that the initial casting solution consists of mHA-DBCO, mHA-CS, and therapeutic aptamer. The microneedles are modified by the CS and the aptamers used as therapeutic agents are incorporated into the CS modified microneedles.

2.2.3. Method 2 for Protein Delivery

A DNA aptamer that is capable of physically binding to the protein, was reacted with mHA-DBCO. This reaction resulted in a covalent bond between the polymer and the aptamer to form mHA-Apt. The above procedure as shown in 2.2.1 can be used except the initial casting solution is consisted of mHA-DBCO, mHA-Apt, and protein.

2.2.4. Combined Method

Combination of 2.2.2 and 2.2.3 can be used in combination for delivery of therapeutic aptamers and proteins.

Example 2

2.2.5 General Procedure of Making Microneedle Patches

The polymer microneedles can be fabricated by casting 25 L of HA-Azide (0.05%) and 25 µL of HA-DBCO (0.05%) The microneedle mold is placed in a vacuum chamber for 10 minutes and then centrifuged for 10 minutes at 3000 RCF (relative centrifugal force). Excess polymer may be removed and the process may be repeated three times to ensure all the microneedle cavities are full. Then, 100 µL of HA (4 wt %) was cast to form the microneedle shafts followed by the casting of PVA/PVP to form the microneedle base.

2.2.6 Method 2 for Delivery of Therapeutic Aptamers

An azide-modified complementary sequence (CS) that is capable of physically binding to the therapeutic aptamer, was reacted with HA-DBCO. It resulted in a covalent bond between the polymer and CS (HA-CS). The above procedure, as shown in 2.2.5, was used except the initial casting solution consisted of HA-DBCO, HA-CS, and a therapeutic aptamer. Incorporation of aptamers used as therapeutic agents into complementary sequence modified microneedles is achieved.

2.2.7 Method 2 for Protein Delivery

Azide-modifed DNA aptamer that is capable of physically binding to the protein, is reacted with HA-DBCO. The reaction results in a covalent bond between the polymer and aptamer (HA-Apt). The above procedure as shown in 2.2.5 can be used except the initial casting solution is consisted of HA-DBCO, HA-Apt, and protein. Incorporation of and proteins into aptamer-functionalized microneedles is achieved for protein delivery.

2.2.8. Combined Method

Combination of 2.2.6 and 2.2.7 can be used in combination for delivery of therapeutic aptamers and proteins.

A More General Description of the Mechanism Underlying Method 1 and Method 2

According to method 1, aptamers are applied to functionalize nanoparticles. Aptamer functionalized nanoparticles will then be mixed with the target protein to enable binding. During the mixing and incubation of the solution, aptamers will bind to the proteins. During this procedure, polymers can be crosslinked or not crosslinked. Then the solution will be cast onto the PDMS mold.

Figure 2A:
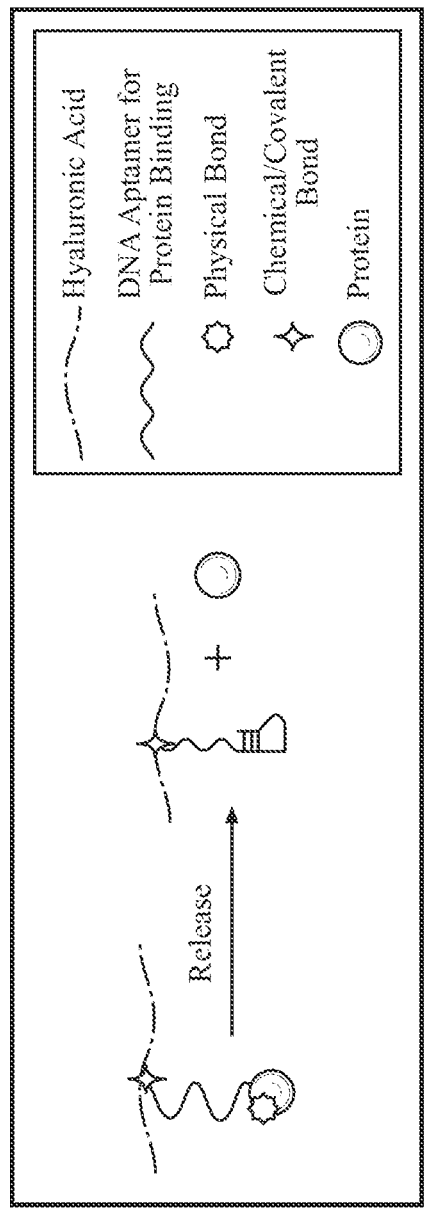
FIG. 2A is a schematic showing the mechanism of protein delivery using aptamers.
Figure 2B:
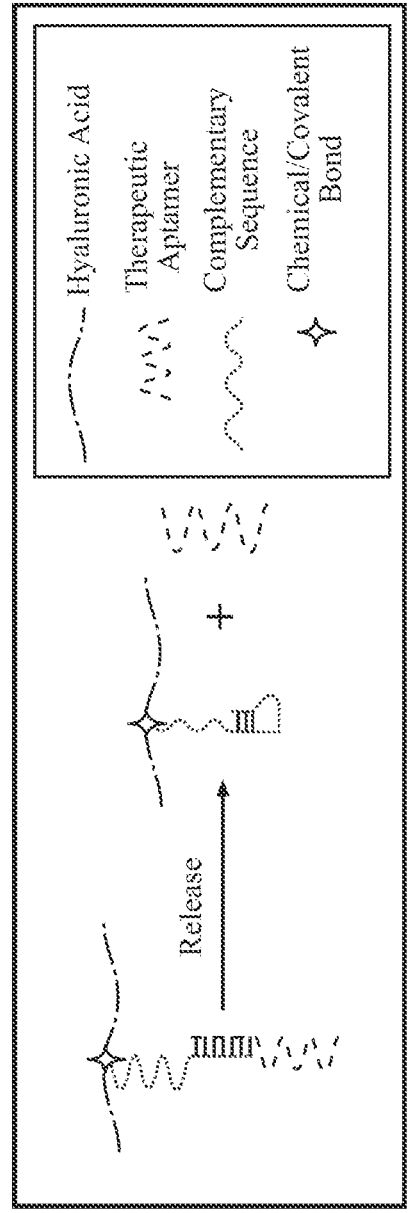
FIG. 2B is a schematic showing the mechanism of delivery of therapeutic aptamers using a complementary sequence.

The microneedles fabricated according to method 2 may be used to deliver protein or therapeutic aptamers, which are shown in FIGS. 2A and 2B.

First, the microneedles fabricated using method 2 may be used to delivery aptamers which are used as therapeutic agents. In this case, a complementary sequence is chemically conjugated to the polymer matrix of the microneedles as the binders of the aptamers. Then, the aptamers are physically bound to the complementary sequence. Over time, the aptamers can be released from the complementary sequence and delivered to a target site when the microneedles are inserted into the target site. The release of the aptamers is a sustained release due to the hybridization of the aptamer to the complementary sequence (dissociation of the aptamer from the complementary sequence). The degree of hybridization can be controlled by modifying the number of base pairs of the CS and aptamer duplex. The aptamers can be released prior to dissolution or degradation of the microneedles.

Second, the microneedles fabricated using method 2 may be used to deliver protein. In this case, the aptamers are chemically conjugated with the polymer matrix of the microneedles such as a hyaluronic acid. The aptamers in this case are immobilized. The microneedles in this case are said to be aptamer-functionalized. The aptamer-functionalized polymer will be mixed with the target protein to enable binding. During the mixing and incubation of the solution, aptamers will bind to the target protein. During this procedure, polymers will be crosslinked. Over time, proteins are dissociated from the aptamers for slow protein release. The protein release profile is mainly governed by the aptamer-protein binding strength (affinity). The binding effect is also affected by the protein concentration, aptamer concentration, and the ion concentration. These concentrations will change over time causing protein dissociation. The protein is constantly binding and re-binding with the aptamer. An aptamer with a high affinity will be able to hold on to the protein for a longer time than a lower affinity aptamer. The aptamer is "anchored" to the microneedle to provide a high local concentration of binding sites of the protein, providing a "slow" protein release. The crosslinked, aptamer-functionalized polymer is also gradually hydrolyzed and/or dissolved in the body, which may facilitate the release kinetics of loaded proteins.

In some embodiments, the tips, the shafts and the bases of the microneedle are crosslinked. After microneedle tips are inserted inside the target diseased site, with time, the crosslinked matrix will be gradually degraded and/or dissolved in the body. The degradation and dissolution depends on enzymatic hydrolysis and swelling of the microneedle tips. Preferably, only the tips of the microneedles are crosslinked. Thus, right after the microneedles are inserted into the target site, the tips will remain at the application site and the bases/shafts of microneedles will be removed/dissolved after the insertion of the microneedles.

FIG. 2C is a schematic diagram showing the mechanisms in FIGS. 2A and 2B combined to deliver therapeutic aptamers and protein.

Below is an example of using hyaluronic acid to make microneedles and using aptamer-functionalized microneedles to deliver therapeutic agents, for example VEGF. Different polymers may be used to realize the same goal.
  a. Hyaluronic acid will be functionalized with chemical moieties for crosslinking and aptamer conjugation.
  b. Hyaluronic acid will be reacted with the aptamer; resulting in aptamer-functionalized hyaluronic acid.
  c. Hyaluronic acid functionalized with aptamer will be mixed with the target protein (VEGF).
  d. After incubating with VEGF for a certain period of time, the solution will be cast onto the PDMS mold. Then vacuum and centrifugation will be applied to push the solution to the tips.
  e. Next, hyaluronic acid will be crosslinked in the tips.
  f. Hyaluronic acid, without any chemical modifications, will be added to fabricate the remaining microneedle shaft and base plate.
  g. After drying, a microneedle patch will be obtained.
  h. The patch will be inserted in the skin, resulting in the deposition of the tip in the skin. The tip contains the crosslinked, aptamer-functionalized hyaluronic and VEGF.
  i. Since the microneedle shaft and base plate are composed of hyaluronic acid, they will dissolve upon contact with the bodily fluids.
  j. Crosslinked hyaluronic acid will be gradually hydrolyzed and dissolved in the body to slowly release drugs after the microneedle insertion. This window of time is much longer than that in step i.

Delivery of Therapeutic Agents to Heart Using Microneedles

The microneedles fabricated using the methods of the present invention can be used to deliver therapeutic agents into the heart for treatment of heart diseases. Any therapeutic agents including aptamers, proteins, siRNA, microRNA, small drugs, or their combinations, etc. can be delivered using this method. Any microneedles that can be used to deliver agents, including but not are limited to the microneedles fabricated using the method of the present invention, can be used for microneedle heart therapy.

In one embodiment, polymer microneedles are microneedles functionalized with DNA or RNA aptamers as the binding sites for the target proteins (growth factors, cytokines, peptides) and used to control the release of proteins.

Using Polymer Microneedles for Skin Therapy or Eye Therapy (e.g., Hair Loss)

The microneedles fabricated using the methods of the present invention can be used to deliver therapeutic agents into the skin or eye.

In one example, the microneedles can be loaded with vascular endothelial growth factor (VEGF) and would be a great option for the local delivery of VEGF for promotion of hair growth.

In this embodiment, microneedles are fabricated with aptamer-functionalized polymer as the binding sites for the VEGF. The aptamer-functionalized polymer microneedles are inserted locally into the target tissue, e.g., scalp tissue. VEGF will release locally at the target site over time due to dissociation from the aptamers. The tips of the microneedles will remain at the application site and degrade or dissolve over time. The base/shaft of the microneedles will be removed/dissolved after the insertion of the microneedles upon the contact with bodily fluids.

Local Aptamer Delivery for Blocking VEGF using Polymer Microneedles

The microneedles of the present invention may be used for creating polymer microneedles capable of delivering DNA aptamers locally to inhibit the function of vascular endothelial growth factor (VEGF). After the microneedles are inserted into the target site, the aptamers will be released over time due to the dissociation from the complementary sequence, generating a sustained release of anti-VEGF aptamer. Once in contact with a physiological solution, the crosslinked polymer microneedles will gradually dissolve, generating a local concentration of anti-VEGF aptamer in the surrounding local microenvironment. Aptamer in a tissue phantom reduces VEGF-mediated endothelial cell tube formation. Thus, aptamer-loaded polymer microneedles in accordance with the present invention hold great potential as a therapeutic tool for the treatment of human diseases resulting from protein overexpression.

Characterization of Microneedles

According to an embodiment of the present invention, the microneedles may be an array of microneedles. The microneedle array may consist of 5×5 to 200×200 microneedles. A preferred range depends on the size of each microneedle and varies for different applications. For example, the microneedle array may consist of 10×10 microneedles for skin treatment and 50×50 microneedles for heart treatment. The microneedles may take the form of pyramidal structures with a pointed upper end and a square base that is larger than the pointed upper end. The microneedles may take the form of conical structures with a pointed upper end and a circular base larger than the pointed upper end. The height of the microneedles may be in the range of 50 μm-2000 μm for skin treatment and 50 μm-30000 μm for heart treatment. The width or diameter of the base to the height ratio may be between 1:2 and 1:10. The tip-to-tip distance of the microneedles may be in the range of 100-2000 μm.

Figure 1A:
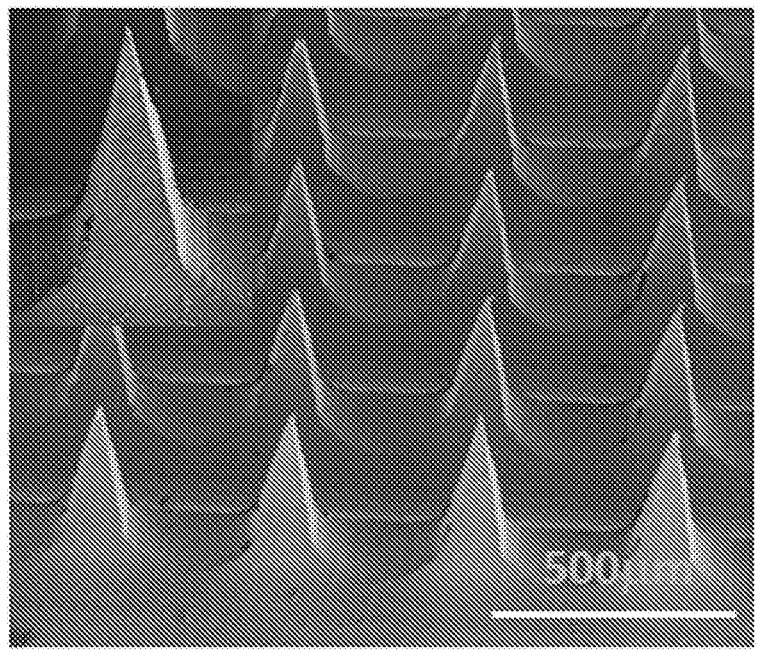
FIG. 1A is a scanning electron microscopy image of a microneedle array with inset for a single microneedle showing examination of microneedle morphology.
Figure 1B:
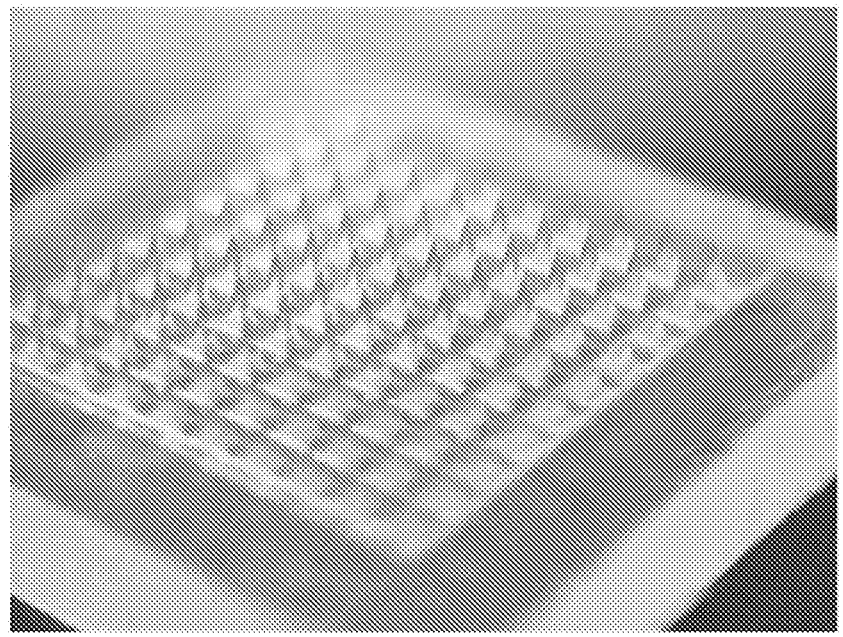
FIG. 1B is a bright-field microscopy image of the microneedle array showing examination of microneedle morphology.

FIG. 1A shows a scanning electron microscopy image of a microneedle array. Inset is a single microneedle. FIG. 1B shows a bright-field microscopy image of the microneedle array.

FIG. 5A is a bright-field image of the microneedles loaded with nanoparticles. Inset is a fluorescent image of a microneedle loaded with nanoparticles. FIG. 5B shows nanoparticle deposition after the microneedles are inserted into a tissue phantom.

FIG. 6A is a bright-field image of protein-loaded microneedle array. The protein is bovine serum albumin (BSA). Inset is a fluorescent image of a microneedle loaded with labelled-BSA. FIG. 6B is a fluorescent image of mouse skin after the treatment using protein-loaded microneedles. FIG. 6C is a cross-sectional image of mouse skin treated with microneedles showing DAPI and labelled BSA. This image shows that the stratum corneum was successfully disrupted, enabling BSA transport into the epidermis. FIG. 6D is a confocal microscopy image of the microneedle treated skin, depth is approximately 30 μm.

Measurement of the Mechanical Strength of Microneedle Arrays

As mechanical strength is important to microneedles in real applications, we examined whether the presence of aptamers in the microneedle matrix would cause any effect on the mechanical strength of microneedles. The mechanical strength of microneedles with and without anti-VEGF DNA aptamer was evaluated using an axial compression instrument (Instron 5960, Norwood, MA). A movable head equipped with a 10N load cell was preset to a maximum extension of 600 μm and a compression rate of 1.1 mm/s before delivering an axial force perpendicular to the microneedle array. The applied force was measured from the point of contact until needle failure, a point characterized by a discontinuity or plateau observed using Bluehill® software. The tip regions of the microneedles bent after a force normal to the microneedle array was applied until a 300 μm compressive force corresponding to ~5.6 N.

Figure 1C:
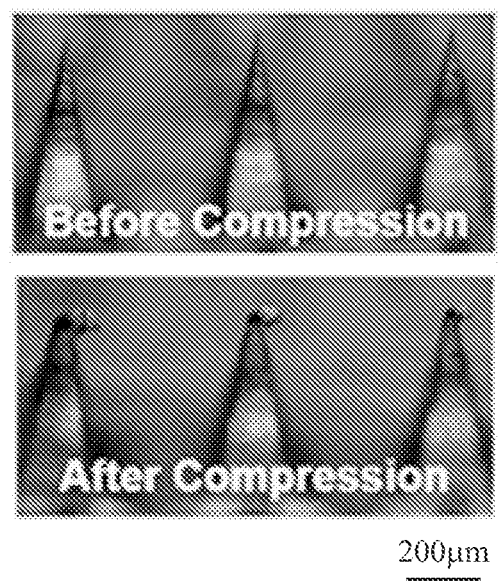
FIG. 1C is images and a graph showing microneedle mechanics during compression testing.
Figure 1C:
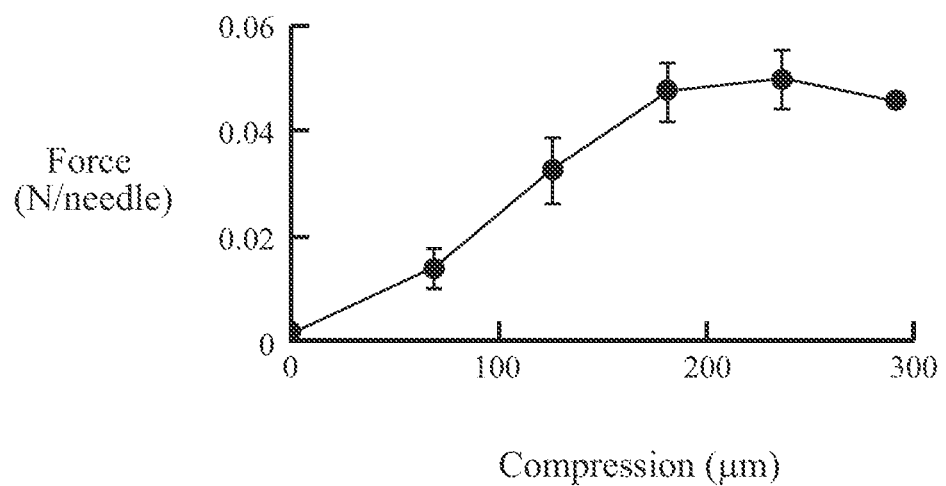

The resultant stress-strain relationship was plotted and the average fracture force per microneedle was calculated from the maximal fracture force divided by the total number of microneedles in the microneedle array. The stress-strain profiles show that the PVP/PVA microneedles and the aptamer-loaded PVP/PVA microneedles had a fracture force at 0.054 N/needle and 0.053 N/needle, respectively, as seen in FIG. 1C. Moreover, these stress-strain profiles nearly overlapped, demonstrating that the presence of aptamers in the microneedles did not affect the mechanical strength of the microneedles.

The presence of anti-VEGF aptamer in the polymer matrix did not change the apparent mechanical strength of the microneedles.

Examination of the Dissolution of Microneedle Arrays

Figure 1D:
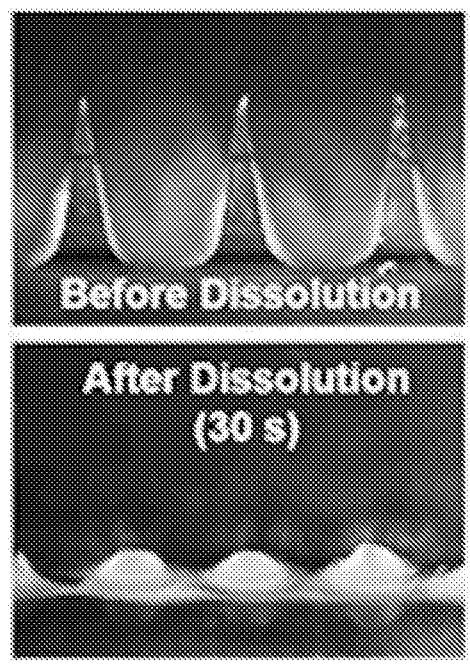
FIG. 1D is images and a graph showing the dissolution kinetics of the microneedles.
Figure 1D:
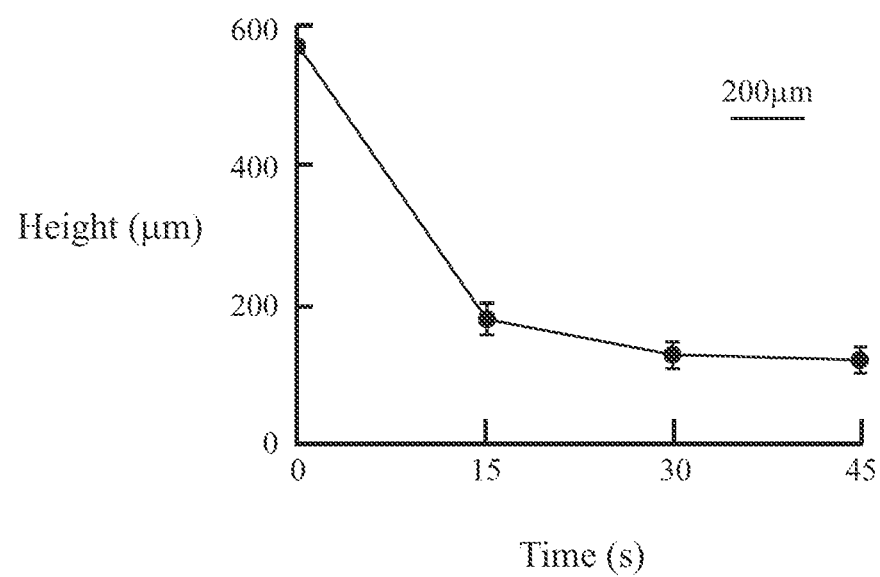

To ensure adequate aptamer delivery, the microneedles need to be dissolvable or degradable in aqueous solutions. Both PVA and PVP are highly hydrophilic. To determine the dissolution of the polymer microneedles, 66 μL of agarose (1% in PBS) was cast into a cylindrical mold and cooled to form an agarose disk with dimensions of 5 mm×2 mm in radius and thickness, respectively. The PVA/PVP microneedle arrays were inserted into the agarose disk that was used herein as a tissue phantom. After a predetermined time interval (15, 30 or 45 seconds), the polymer microneedle arrays were removed and immediately placed in an 80° C. oven to dry the surface of the microneedles before imaging. The microneedles were imaged under an Olympus MVX10 microscope (Center Valley, PA) and quantified using ImageJ. Within 15 s, the height of the microneedles decreased by 70%, as shown in FIG. 1D. After 30 s, the tip regions of the microneedles virtually completely disappeared with only the microneedle bases remaining. These results demonstrate that the aptamer-loaded PVA/PVP microneedles are highly dissolvable.

FIG. 7A is an image of H &E stained mouse skin after treatment with VEGF-loaded microneedles. FIG. 7B is an image of the dorsal region of the mouse after treatment with VEGF-loaded microneedles. FIG. 7C is an image of H &E stained mouse skin after treatment with pure PVA/PVP microneedles (control). FIG. 7D is an image of the dorsal region of the mouse after treatment with VEGF-loaded microneedles. The VEGF-loaded microneedles were able to stimulate hair growth on the dorsal region of the mice after 5 days. This is supported by the white-hair clearly visible in FIG. 4B. Upon further examination, the tissue collected from the VEGF-loaded microneedle treated group contained more hair follicles than the control group (FIGS. 4A and 4C). Thus, VEGF delivered via microneedles can stimulate hair regrowth.

FIG. 8A shows a fluorescent image of the mouse heart after microneedle treatment. FIG. 8B is an image of the outer boundary of the heart after microneedle treatment, showing labelled-BSA was successfully deposited below the outer boundary of the heart.

As will be clear to those of skill in the art, the embodiments of the present invention illustrated and discussed herein may be altered in various ways without departing from the scope or teaching of the present invention. Also, elements and aspects of one embodiment may be combined with elements and aspects of another embodiment. It is the following claims, including all equivalents, which define the scope of the invention.

The invention claimed is:

1. A method of providing therapeutic treatment by delivering protein locally to a target site using microneedles, the method comprising the steps of:
   providing aptamer-functionalized microneedles by:
     reacting an aptamer with a polymer forming a covalent bond between the polymer and the aptamer;
     forming microneedle patches using an initial casting solution consisting of the polymer, the covalent bond and the protein, thereby loading the protein into the microneedles, each microneedle including a tip, a shaft and a base;
   physically binding the protein to the aptamer;
   inserting the microneedles into the target site such that the tips and shafts are embedded into the target site and the bases are on a surface of the target site; and
   sustainably releasing the protein to the target site due to dissociation of the protein from the aptamer over time.

2. The method of providing therapeutic treatment according to claim 1, further comprising dissolution or degradation of the microneedles, the dissociation of the protein from the aptamer taking place prior to, during or after the dissolution or degradation of the microneedles.

3. The method of providing therapeutic treatment according to claim 1, wherein the polymer is the hyaluronic acid functionalized with methacrylate and DBCO (mHA-DBCO), the aptamer is azide-modified DNA aptamer and the covalent bond is mHA-Apt.

4. The method of providing therapeutic treatment according to claim 1, wherein the polymer is the hyaluronic acid functionalized with DBCO (HA-DBCO), the aptamer is azide-modified DNA aptamer and the covalent bond is HA-Apt.

5. The method of providing therapeutic treatment according to claim 1, wherein the aptamer is loaded into the tips, shafts or bases of the microneedles.

6. The method of providing therapeutic treatment according to claim 2, wherein releasing the aptamer is by dissolution or degradation of the tips, shafts and bases of the microneedles.

7. The method of providing therapeutic treatment according to claim 1, wherein the target site is heart tissue, skin or eye.

* * * * *